United States Patent
Dong et al.

(10) Patent No.: US 11,771,773 B2
(45) Date of Patent: Oct. 3, 2023

(54) PHARMACEUTICAL PREPARATION CONTAINING POLYETHYLENE GYLCOL LOXENATIDE AND PREPARATION METHOD THEREOF

(71) Applicant: Jiangsu Hansoh Pharmaceutical Group Co., Ltd., Lianyungang (CN)

(72) Inventors: Li Dong, Lianyungang (CN); Ge Wang, Lianyungang (CN); Di Hu, Lianyungang (CN); Yundong Sun, Lianyungang (CN); Hengli Yuan, Lianyungang (CN)

(73) Assignee: Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 316 days.

(21) Appl. No.: 16/341,616

(22) PCT Filed: Oct. 16, 2017

(86) PCT No.: PCT/CN2017/106355
§ 371 (c)(1),
(2) Date: Apr. 12, 2019

(87) PCT Pub. No.: WO2018/068770
PCT Pub. Date: Apr. 19, 2018

(65) Prior Publication Data
US 2022/0088205 A1    Mar. 24, 2022

(30) Foreign Application Priority Data
Oct. 14, 2016    (CN) .......................... 201610900107.0

(51) Int. Cl.
| | | |
|---|---|---|
| A61K 47/60 | (2017.01) |
| A61K 9/00 | (2006.01) |
| A61K 38/17 | (2006.01) |
| A61K 47/12 | (2006.01) |
| A61K 47/14 | (2017.01) |
| A61K 47/26 | (2006.01) |

(52) U.S. Cl.
CPC ............ A61K 47/60 (2017.08); A61K 9/0019 (2013.01); A61K 38/177 (2013.01); A61K 47/12 (2013.01); A61K 47/14 (2013.01); A61K 47/26 (2013.01)

(58) Field of Classification Search
None
See application file for complete search history.

(56) References Cited

FOREIGN PATENT DOCUMENTS

| | | |
|---|---|---|
| CN | 101366692 A | 2/2009 |
| CN | 1016422562 * | 1/2012 |
| CN | 102786590 A | 11/2012 |
| JP | 2009/526080 * | 1/2009 |
| WO | WO-2018068770 A1 | 4/2018 |

OTHER PUBLICATIONS

"International Application No. PCT/CN2017/106355, International Search Report and Written Opinion dated Jan. 19, 2017", (dated Jan. 19, 2017), 9 pgs.

Ma, Xiaolan, "Pharmacokinetics, Pharmacodynamics, Tolerability, and Safety of Polyethylene Glycol Loxenatide Injection (PEX-168) in Type 2 Diabetes", China Master Theses Full-Text Database, Medicine and Public Health, No. 10, ISSN: 1674-0246, part 1, Section 1.1 (2012), (Oct. 15, 2012), 5 pgs.

"European Application No. 17861073.9, European Search Report dated Apr. 14, 2020", (dated Apr. 14, 2020), 6 pgs.

Yang, Guang-Ran, et al., "Pharmacokinetics and pharmacodynamics of a polyethylene glycol (PEG-conjugated GLP-receptor agonist once weekly in Chinese patients with type 2 diabetes", Journal of Clinical Pharmacology, vol. 55, No. 2, (Jan. 1, 2015), 152-158.

* cited by examiner

Primary Examiner — Julie Ha
Assistant Examiner — Tara L Martinez
(74) Attorney, Agent, or Firm — Schwegman Lundberg & Woessner, P.A.

(57) ABSTRACT

Disclosed are a GLP-1-mimicking pharmaceutical composition for treating type 2 diabetes and a preparation method thereof, wherein the pharmaceutical composition contains polyethylene glycol loxenatide, a physiologically acceptable buffer with the pH of 3.0-7.0, and pharmaceutically acceptable excipients. The pharmaceutical composition has good drug stability.

5 Claims, No Drawings
Specification includes a Sequence Listing.

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<221> NAME/KEY: PEPTIDE
<222> LOCATION: (1)..(39)
<223> OTHER INFORMATION: A synthetic polyethylene glycol loxenatide
      sequence
<220> FEATURE:
<222> LOCATION: (2)..(2)
<223> OTHER INFORMATION: d-alanine
<220> FEATURE:
<221> NAME/KEY: BINDING
<222> LOCATION: (39)..(39)
<223> OTHER INFORMATION: mPEG2-Lys-MAL
<220> FEATURE:
<221> NAME/KEY: AMIDATION
<222> LOCATION: (39)..(39)
<220> FEATURE:
<221> NAME/KEY: UNSURE
<222> LOCATION: (14)..(14)
<223> OTHER INFORMATION: The 'Xaa' at location 14 stands for Nle.

<400> SEQUENCE: 1

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

PHARMACEUTICAL PREPARATION CONTAINING POLYETHYLENE GYLCOL LOXENATIDE AND PREPARATION METHOD THEREOF

PRIORITY CLAIM TO RELATED APPLICATIONS

This application is a U.S. national stage filing under 35 U.S.C. § 371 from International Application No. PCT/CN2017/106355, filed on 16 Oct. 2017, and published as WO2018/068770 on 19 Apr. 2018, which claims the benefit under 35 U.S.C. 119 to Chinese Application No. 201610900107.0, filed on 14 Oct. 2016, the benefit of priority of each of which is claimed herein, and which applications and publication are hereby incorporated herein by reference in their entirety.

FIELD OF THE INVENTION

The present invention relates to the field of polypeptide pharmaceutical formulations. In particular, the present invention relates to a pharmaceutical formulation comprising polyethylene glycol loxenatide and a process for the same.

BACKGROUND OF THE INVENTION

Diabetes is the third largest disease in the world, and death from diabetes is the fourth leading cause of death in the world today. Diabetes is usually divided into type 1 (insulin-dependent) diabetes and type 2 (non-insulin-dependent) diabetes. Among them, type 2 diabetes accounts for about 90% of the total number of diabetic patients. The glycemic control of type 2 diabetes tends to deteriorate progressively over time; when diet control and exercise therapy fail, a new hypoglycemic agent intervention treatment is required on an average of every 3-4 years to achieve or maintain good glycemic control. Ultimately, even in the current case of combination drug therapy and/or insulin therapy, a significant proportion of patients are unable to achieve good glycemic control, and certain drugs may cause side-effects such as hypoglycemia, liver toxicity, induced obesity and water and salt retention in the body.

In April 2005, the FDA approved Byetta (common name Exenatide) to be marketed in the United States. This is the first approved new treatment for type 2 diabetes that mimics GLP-1. The amino acid sequence of Exenatide partially overlaps with the human GLP-1 sequence and has been shown to bind to the human GLP-1 receptor and activate the receptor in vitro. This result leads to an increase in glycemic-dependent insulin synthesis and in the secretion of insulin by pancreatic beta cells in vivo by acting on cAMP and/or other intracellular signaling pathways. Promoting beta cell secretion of insulin by Exenatide is glycemic dependent. When injected in vivo, Exenatide produces a similar effect to the main hypoglycemic effect of GLP-1.

Compared with natural GLP-1, Exenatide has the greatest advantage that it cannot be rapidly degraded by dipeptidyl peptidase IV in vivo and thus has a longer half-life and stronger biological activity. Although Exenatide has more advantages than the previous hypoglycemic drugs, as a peptide drug, its half-life in human body is still only 2 to 3 hours, and it should be administered via subcutaneous injection twice a day, which directly affects patient compliance.

By modifying Exenatide, it can further resist the rapid degradation of DPP-4 in vivo. Meanwhile, we also noticed that after modification with polyethylene glycol (PEG), many protein and peptide drugs can reduce the toxicity of drugs, prolong the half-life and action duration of drugs, and increase the bioavailability thereof, thereby improving the therapeutic effect of drugs, under the premise of ensuring efficacy, prolonging the dosing interval, reducing the number of administrations can improve patient compliance. Based on the above two points, we make amino acid modification and PEGylation to Exenatide to obtain polyethylene glycol loxenatide. The clinical results show that the half-life (t½) of polyethylene glycol loxenatide is up to 80 hours, which is much higher than Exenatide. Good glucose-dependent insulinotropic function is shown in normal rats and is dose dependent. After polyethylene glycol loxenatide is injected subcutaneously once every three days in type 2 diabetes db/db mice, the random, fasting blood glucose and serum fructosamine levels in mice are significantly reduced, the glucose tolerance is improved, and the body weight is reduced. The efficacy is comparable to that of Exenatide which is injected subcutaneously twice a day.

This suggests that polyethylene glycol loxenatide has a good hypoglycemic effect in classical diabetic model animals. It has an obvious therapeutic effect on type II diabetes, and can avoid adverse reactions of hypoglycemia and weight gain. Compared with Exenatide, it has long-lasting characteristics, which significantly reduces the number of invasive drug administrations and has a good development prospect.

However, although peptide drugs have been widely used in clinical research or treatment processes, a stable and high-quality therapeutic polypeptide drug which can be industrially produced remains a major challenge for researchers. Different preparation processes and addition of different kinds of stabilizers are often used in the development of peptide pharmaceutical formulations to improve their stability. For parenteral formulations, the shelf life is at least one year or longer. In view of the temperature changes and oscillations during the transport of the sample, it is necessary to improve the stability of polyethylene glycol loxenatide injection.

SUMMARY OF THE INVENTION

An object of the present invention is to provide a stable pharmaceutical composition of polyethylene glycol loxenatide.

Specifically, the object of the present invention is mainly achieved by the following embodiments.

A pharmaceutical composition of polyethylene glycol loxenatide comprises polyethylene glycol loxenatide as an active ingredient, a buffer and an isosmotic regulator, wherein the polyethylene glycol loxenatide has a structure of (SEQ ID NO: 1)

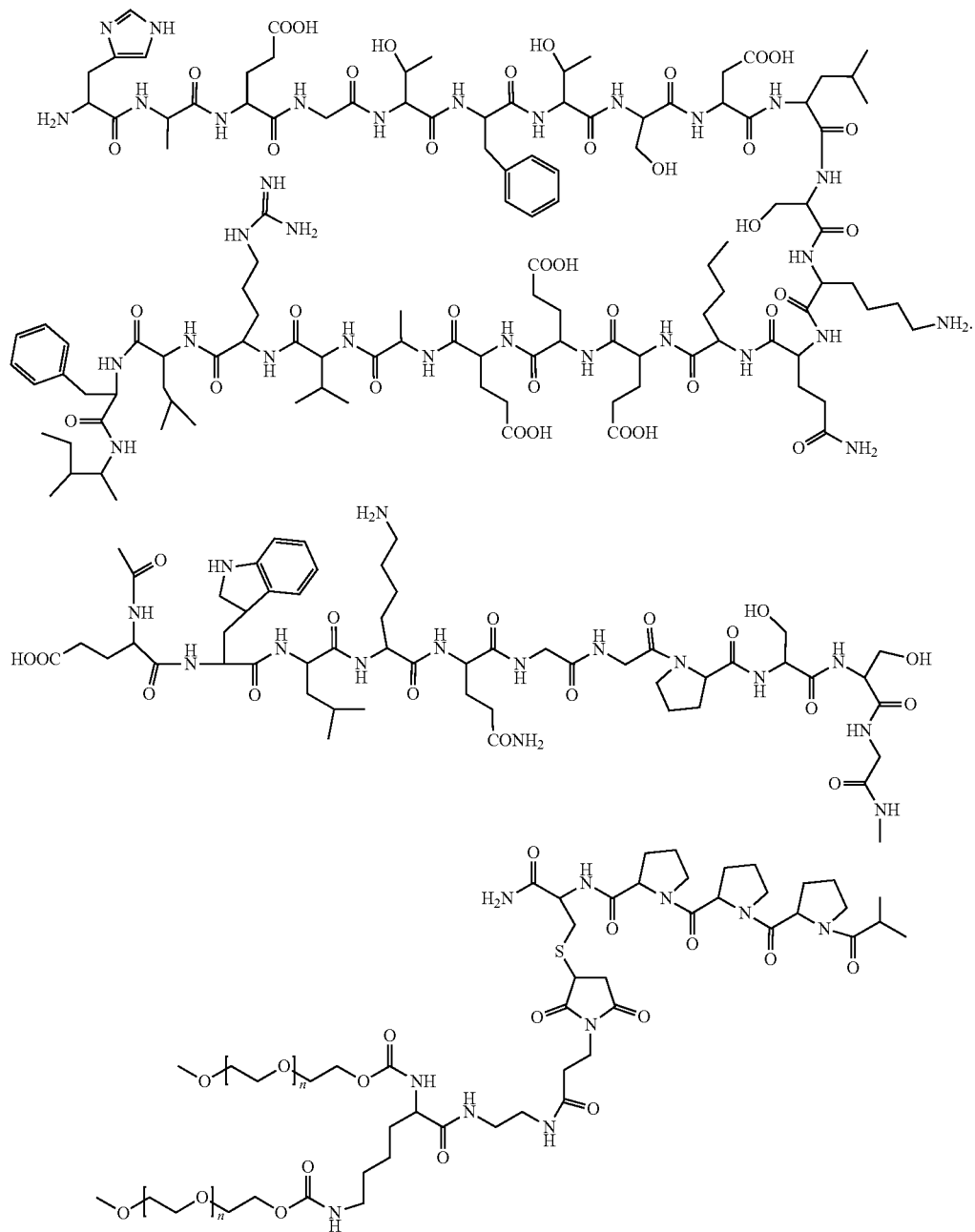

Preferably, the concentration of the polyethylene glycol loxenatide is 0.1 mg/mi to 100 mg/ml, preferably 0.1 mg/ml to 20 mg/mi.

Preferably, the pharmaceutical composition of polyethylene glycol loxenatide is a polyethylene glycol loxenatide injection comprising 0.05% to 5.0% (W/V) of polyethylene glycol loxenatide, 0.1% to 5.0% (W/V) of a buffer salt, and 1.0% to 10.0% (W/V) of an isosmotic regulator, wherein the unit of W/is g/mL.

Preferably, the polyethylene glycol loxenatide injection comprises 0.1% to 2% (W/V) of polyethylene glycol loxenatide, 0.3% to 3.0% (WY) of a buffer salt, and 2.0% to 5.0% (W/V) of an isosmotic regulator.

Preferably, the polyethylene glycol loxenatide injection comprises 0.1% to 2% (W/V) of polyethylene glycol loxenatide, 0.5% to 1.5% (W/V) of a buffer salt, and 2.0% to 5.0% (W/V) of an isosmotic regulator.

Preferably, the buffer is selected from the group consisting of a phosphate buffer, an acetate buffer, a citrate buffer, a carbonate buffer, a tartrate buffer, a Tris buffer and a histidine buffer, preferably an acetate buffer or a phosphate buffer, wherein the acetate buffer comprises acetic acid and acetate, and the acetic acid is a 36% to 38% acetic acid solution.

Preferably, the isosmotic regulator is one or more selected from the group consisting of sodium chloride, mannitol, sorbitol, glycerin, glucose and xylitol, preferably mannitol or sodium chloride.

Preferably, the polyethylene glycol loxenatide injection comprises 0.1% to 2% (W/V) of polyethylene glycol loxenatide, 0.5% to 1.5% (W/V) of acetic acid/sodium acetate, and 2.0% to 5.0% (W/V) of mannitol.

More preferably, the polyethylene glycol loxenatide injection comprises 0.1% to 0.5% (W/V) of polyethylene glycol loxenatide, 0.5% to 1.5% (W/V) of acetic acid/sodium acetate, and 2.0% to 5.0% (W/V) of mannitol.

The pharmaceutical composition of polyethylene glycol loxenatide optionally further comprises a surfactant or a stabilizer.

The surfactant is selected from the group consisting of polysorbate 80, polysorbate 20, polysorbate 40, polysorbate 60 and poloxamer 188; preferably polysorbate 80 or poloxamer 188. The amount of the surfactant is 0.01% to 10% (W/V), preferably 0.05% to 5% (W/V).

The stabilizer is selected from the group consisting of L-glutathione. L-arginine, L-histidine, arginine, sodium thiosulfate, sodium sulfite and sodium hydrogen sulfite, preferably L-glutathione. The amount of the stabilizer is 0.01% to 5.0% (w/v), preferably 0.02% to 0.5% (w/v).

Preferably, the weight ratio of the polyethylene glycol loxenatide to the buffer salt is 1:0.1 to 10, preferably 1:0.3 to 5.

Preferably, the weight ratio of the free acid to the salt thereof in the buffer salt is from 1:1 to 10, preferably from 1:2 to 5.

Preferably, the weight ratio of the polyethylene glycol loxenatide to the isosmotic regulator is 1:0.1 to 100, preferably 1:1 to 20.

Preferably, the pharmaceutical composition has a pH in the range of 3.0 to 7.0, preferably 4.0 to 6.0.

Another object of the present invention is to provide a method for preparing the pharmaceutical composition comprising the steps of dissolving a buffer salt and an isosmotic regulator in water for injection; adding activated carbon, and then filtering the mixture to remove the activated carbon to obtain an intermediate solution; dissolving polyethylene glycol loxenatide in the above solution under stirring, filtering and dispensing the resulting composition.

Preferably, the low temperature condition is between 2° C. and 25° C.

Preferably, the intermediate solution has an oxygen content of ≤10%.

Preferably, the pharmaceutical composition is sterile filtered, dispensed, and nitrogen filled.

Preferably, the intermediate solution is formulated under nitrogen atmosphere.

Preferably, the intermediate solution is subjected to nitrogen pressure filtration.

Preferably, the filling process is carried out under nitrogen atmosphere.

Preferably, the pharmaceutical composition is dispensed using a vial.

Preferably, the pharmaceutical composition is dispensed using a prefilled syringe.

Preferably, the pharmaceutical composition is dispensed using a portable bottle.

The present invention can obtain a stable pharmaceutical composition of polyethylene glycol loxenatide by screening the components in the formula and controlling the proportion of each component without adding other auxiliary materials. Moreover, the stability of the polyethylene glycol loxenatide formulation is improved by controlling the oxygen content in the drug solution to be ≤10%.

DETAILED DESCRIPTION OF THE INVENTION

The present invention is further illustrated by the following examples, which should not to be construed as further limitation. Those skilled in the art will appreciate that the particular methods and results described herein are merely illustrative.

Example 1

| Polyethylene glycol loxenatide | 1.06 g |
| Acetic acid | 0.8 g |
| Sodium acetate | 2.5 g |
| Mannitol | 10.5 g |
| Water for injection | up to 500 ml |

The prescription amount of 0.8 g of acetic acid and 2.5 g of sodium acetate were weighed and dissolved in 400 ml of water for injection, and then added with 10.5 g of mannitol, stirred and dissolved. The above solution was added with 0.1% activated carbon and kept at 60° C. in a water bath for 15 minutes. The mixture was filtered while it was hot to remove activated carbon. The subsequent filtrate was cooled to 20° C., and then added with the prescription amount of 1.05 g of polyethylene glycol loxenatide, slowly stirred and dissolved. The pH of the drug solution was adjusted to 3.0, 4.0, 6.0, 7.0 and 10.0 with acetic acid or sodium hydroxide, respectively. The above drug solution was added with water for injection to the constant volume of 500 ml. Finally, the drug solution was filtered through a 0.22 μm microporous membrane and dispensed into vials. The vials were filled with nitrogen and then stoppered and capped. The stability of the samples was investigated at 25° C. and 40° C., respectively. The indicators were appearance, turbidity, related substances and content. The results are shown in Table 1.

TABLE 1

| pH | Time (Month) | Temperature (° C.) | Appearance | Turbidity (NTU) | Total impurity (%) | Content (%) |
|---|---|---|---|---|---|---|
| 3.0 | 0 | / | Colorless clear liquid | 0.6 | 0.98 | 100.0 |
| 4.0 | | | Colorless clear liquid | 0.5 | 0.94 | 100.3 |
| 6.0 | | | Colorless clear liquid | 0.5 | 1.01 | 99.7 |
| 7.0 | | | Colorless clear liquid | 0.6 | 1.02 | 99.8 |
| 10.0 | | | Colorless clear liquid | 0.6 | 1.11 | 99.7 |
| 3.0 | 6 | 25 | Colorless clear liquid | 1.2 | 1.65 | 98.5 |

TABLE 1-continued

| pH | Time (Month) | Temperature (° C.) | Appearance | Turbidity (NTU) | Total impurity (%) | Content (%) |
|---|---|---|---|---|---|---|
| 4.0 | | | Colorless clear liquid | 0.8 | 1.32 | 98.7 |
| 6.0 | | | Colorless clear liquid | 0.7 | 1.28 | 99.1 |
| 7.0 | | | Colorless clear liquid | 0.7 | 1.50 | 98.7 |
| 10.0 | | | Colorless clear liquid | 0.9 | 5.74 | 94.1 |
| 3.0 | 6 | 40 | Colorless clear liquid | 4.3 | 4.10 | 96.4 |
| 4.0 | | | Colorless clear liquid | 1.5 | 2.09 | 98.2 |
| 6.0 | | | Colorless clear liquid | 1.6 | 2.21 | 98.0 |
| 7.0 | | | Colorless clear liquid | 1.8 | 3.57 | 97.4 |
| 10.0 | | | Colorless clear liquid | 3.6 | 20.14 | 77.8 |

Example 2

| | |
|---|---|
| Polyethylene glycol loxenatide | 5.1 g |
| Acetic acid | 1.1 g |
| Sodium acetate | 3.2 g |
| Isosmotic regulator | 12.0 g |
| Water for injection | up to 500 ml |

The prescription amount of 1.1 g of acetic acid and 3.2 g of sodium acetate were weighed and dissolved in 400 ml of water for injection, and then added with the prescription amount of 12.0 g of the isosmotic regulator, stirred and dissolved. The above solution was added with 0.1% activated carbon and kept at 60° C. in a water bath for 15 minutes. The mixture was filtered while it was hot to remove activated carbon. The subsequent filtrate was cooled to 25° C., and then added with the prescription amount of 5.1 g of polyethylene glycol loxenatide, slowly stirred and dissolved. If necessary, the pH of the drug solution was adjusted to about 5.0 with acetic acid or sodium acetate. The above drug solution was added with water for injection to the constant volume of 500 ml. Finally, the drug solution was filtered through a 0.22 μm microporous membrane and dispensed into prefilled syringes. The prefilled syringes were filled with nitrogen and then stoppered and capped. The stability of the samples was investigated at 25° C. and 40° C., respectively. The indicators were appearance, turbidity, related substances and content. The results are shown in Table 2.

TABLE 2

| Isosmotic agent | Time (Month) | Temperature (° C.) | Appearance | Turbidity (NTU) | Total impurity (%) | Content (%) |
|---|---|---|---|---|---|---|
| Sodium chloride | 0 | / | Colorless clear liquid | 0.6 | 1.05 | 99.4 |
| Mannitol | | | Colorless clear liquid | 0.5 | 1.06 | 99.2 |
| Sorbitol | | | Colorless clear liquid | 0.5 | 1.10 | 99.4 |
| Glycerin | | | Colorless clear liquid | 0.9 | 1.33 | 99.0 |
| Xylitol | | | Colorless clear liquid | 0.6 | 1.09 | 99.0 |
| Sodium chloride | 6 | 25 | Colorless clear liquid | 1.0 | 1.67 | 98.4 |
| Mannitol | | | Colorless clear liquid | 0.8 | 1.30 | 99.0 |
| Sorbitol | | | Colorless clear liquid | 1.6 | 1.79 | 98.6 |
| Glycerin | | | Colorless clear liquid | 2.5 | 2.71 | 97.0 |
| Xylitol | | | Colorless clear liquid | 1.8 | 1.81 | 98.1 |
| Sodium chloride | 6 | 40 | Colorless clear liquid | 2.0 | 2.24 | 98.0 |
| Mannitol | | | Colorless clear liquid | 1.5 | 1.97 | 98.5 |
| Sorbitol | | | Colorless clear liquid | 2.8 | 2.94 | 96.8 |

TABLE 2-continued

| Isosmotic agent | Time (Month) | Temperature (° C.) | Appearance | Turbidity (NTU) | Total impurity (%) | Content (%) |
|---|---|---|---|---|---|---|
| Glycerin | | | Colorless clear liquid | 4.1 | 3.04 | 96.7 |
| Xylitol | | | Colorless clear liquid | 3.5 | 2.63 | 97.5 |

Example 3

| | |
|---|---|
| Polyethylene glycol loxenatide | 7.3 g |
| Acetic acid | 0.87 g |
| Sodium acetate | 3.0 g |
| Mannitol | q.s. |
| Water for injection | up to 500 ml |

The prescription amount of 0.87 g of acetic acid and 4.3 g of sodium acetate were weighed and dissolved in 300 ml of water for injection, and then added with 5.0 g, 10 g, 15 g, 25 g, 50 g of mannitol respectively, stirred and dissolved. The above solution was added with 0.1% activated carbon and kept at 60° C. in a water bath for 15 minutes. The mixture was filtered while it was hot to remove activated carbon. The subsequent filtrate was cooled to 25° C., and then added with the prescription amount of 7.3 g of polyethylene glycol loxenatide, slowly stirred and dissolved. If necessary, the pH of the drug solution was adjusted to about 5.5 with acetic acid or sodium acetate. The above drug solution was added with water for injection to the constant volume of 500 ml. Finally, the drug solution was filtered through a 0.22 μm microporous membrane and dispensed into portable bottles. The portable bottles were filled with nitrogen and then stoppered and capped. The stability of the samples was investigated at 25° C. and 40° C., respectively. The indicators were appearance, turbidity, related substances and content. The results are shown in Table 3.

TABLE 3

| Mannitol Weight (g) | Time (Month) | Temperature (° C.) | Appearance | Turbidity (NTU) | Total impurity (%) | Content (%) |
|---|---|---|---|---|---|---|
| 5 | 0 | / | Colorless clear liquid | 0.6 | 1.05 | 99.4 |
| 10 | | | Colorless clear liquid | 0.5 | 1.06 | 90.9 |
| 15 | | | Colorless clear liquid | 0.5 | 1.01 | 99.4 |
| 25 | | | Colorless clear liquid | 0.5 | 1.03 | 99.5 |
| 50 | | | Colorless clear liquid | 0.6 | 1.09 | 99.0 |
| 5 | 6 | 25 | Colorless clear liquid | 0.8 | 1.67 | 98.4 |
| 10 | | | Colorless clear liquid | 0.6 | 1.30 | 99.0 |
| 15 | | | Colorless clear liquid | 0.6 | 1.29 | 99.2 |
| 25 | | | Colorless clear liquid | 0.5 | 1.27 | 99.2 |
| 50 | | | Colorless clear liquid | 0.9 | 1.35 | 98.8 |
| 5 | 6 | 40 | Colorless clear liquid | 1.8 | 2.61 | 97.1 |
| 10 | | | Colorless clear liquid | 0.7 | 2.14 | 97.8 |
| 15 | | | Colorless clear liquid | 0.7 | 2.09 | 97.9 |
| 25 | | | Colorless clear liquid | 0.8 | 2.08 | 98.1 |
| 50 | | | Colorless clear liquid | 1.5 | 2.19 | 97.5 |

Example 4

| | |
|---|---|
| Polyethylene glycol loxenatide | 2.02 g |
| Acetic acid | q.s. |
| Sodium acetate | q.s. |
| Mannitol | 15 g |

The prescription amount of acetic acid and sodium acetate were weighed and dissolved in 200 ml of water for injection, and then added with 15 g of mannitol, stirred and dissolved. The above solution was added with 0.1% activated carbon and kept at 60° C. in a water bath for 15 minutes. The mixture was filtered while it was hot to remove activated carbon. The subsequent filtrate was cooled to 20° C., and then added with the prescription amount of 2.02 g of polyethylene glycol loxenatide, slowly stirred and dissolved. The above drug solution was added with water for injection to the constant volume of 500 ml. Finally, the drug solution was filtered through a 0.22 μm microporous membrane and dispensed into portable bottles. The portable bottles were filled with nitrogen and then stoppered and capped. The stability of the samples was investigated at 25° C. and 40° C., respectively. The indicators were appearance, turbidity, related substances and content. The results are shown in Table 4.

Example 5

| | |
|---|---|
| Polyethylene glycol loxenatide | q.s. |
| Acetic acid | 1.1 g |
| Sodium acetate | 3.5 g |
| Mannitol | q.s. |
| Water for injection | up to 500 ml |

The prescription amount of 1.1 g of acetic acid and 3.5 g of sodium acetate were weighed and dissolved in 420 ml of water for injection, and then added with 10 g, 20 g, or 50 g of mannitol, respectively, stirred and dissolved. The solution was added with 0.1% activated carbon and kept at 60° C. in a water bath for 15 minutes. The mixture was filtered while it was hot to remove activated carbon. The subsequent filtrate was cooled to 15° C., and then added with the prescription amount of 1 g, 10 g or 50 g of polyethylene glycol loxenatide, slowly stirred and dissolved. If necessary, the pH of the drug solution was adjusted to about 5.0 with acetic acid or sodium acetate. The above drug solution was added with water for injection to the constant volume of 500 ml. Finally, the drug solution was filtered through a 0.22 μm microporous membrane and dispensed into vials. The vials were filled with nitrogen and then stoppered and capped. The stability of the samples was investigated at 25° C. and 40° C., respectively. The indicators were appearance, turbidity, related substances and content. The results are shown in Table 5.

TABLE 4

| Acetic acid/Sodium acetate (g) | Time (Month) | Temperature (° C.) | Appearance | Turbidity (NTU) | Total impurity (%) | Content (%) |
|---|---|---|---|---|---|---|
| 0.9/2.5 | 0 | / | Colorless clear liquid | 0.5 | 1.01 | 99.4 |
| 1.1/5.2 | | | Colorless clear liquid | 0.6 | 1.06 | 99.2 |
| 0.9/8.2 | | | Colorless clear liquid | 0.8 | 1.04 | 99.4 |
| 0.9/2.5 | 6 | 25 | Colorless clear liquid | 0.8 | 1.47 | 99.0 |
| 1.1/5.2 | | | Colorless clear liquid | 0.7 | 1.40 | 98.8 |
| 0.9/8.2 | | | Colorless clear liquid | 1.4 | 2.07 | 98.0 |
| 0.9/2.5 | 6 | 40 | Colorless clear liquid | 0.8 | 2.19 | 98.0 |
| 1.1/5.2 | | | Colorless clear liquid | 0.8 | 2.24 | 98.1 |
| 0.9/8.2 | | | Colorless clear liquid | 1.9 | 4.25 | 95.8 |

TABLE 5

| Polyethylene glycol loxenatide (g) | Time (Month) | Temperature (° C.) | Appearance | Turbidity (NTU) | Total impurity (%) | Content (%) |
|---|---|---|---|---|---|---|
| 1 | 0 | / | Colorless clear liquid | 0.5 | 1.01 | 99.4 |
| 10 | | | Colorless clear liquid | 0.7 | 1.01 | 99.2 |
| 50 | | | Colorless clear liquid | 1.0 | 1.03 | 99.2 |
| 1 | 6 | 25 | Colorless clear liquid | 0.6 | 1.21 | 98.7 |
| 10 | | | Colorless clear liquid | 0.7 | 1.32 | 98.6 |
| 50 | | | Colorless clear liquid | 1.6 | 1.84 | 98.2 |
| 0.5 | 6 | 40 | Colorless clear liquid | 0.8 | 2.08 | 98.3 |
| 10 | | | Colorless clear liquid | 0.9 | 2.10 | 98.1 |
| 50 | | | Colorless clear liquid | 2.7 | 3.12 | 97.1 |

Example 6

| | |
|---|---|
| Polyethylene glycol loxenatide | 2.06 g |
| Acetic acid | 0.9 g |
| Sodium acetate | 2.7 g |
| Mannitol | 12.5 g |
| Water for injection | up to 500 ml |

Formula 6-1:

The prescription amount of 0.9 g of acetic acid and 2.7 g of sodium acetate were weighed and dissolved in 400 ml of water for injection, and then added with 12.5 g of mannitol, stirred and dissolved. The above solution was added with 0.1% activated carbon and kept at 60° C. in a water bath for 15 minutes. The mixture was filtered while it was hot to remove activated carbon. The subsequent filtrate was cooled to 20° C., and then added with the prescription amount of 2.06 g of polyethylene glycol loxenatide, slowly stirred and dissolved. The pH of the drug solution was adjusted to pH 3.0, 4.0, 6.0, 7.0 and 10.0 with acetic acid or sodium hydroxide, respectively. The above drug solution was added with water for injection to the constant volume of 500 ml. Finally, the drug solution was filtered through a 0.22 μm microporous membrane and dispensed into vials. The vials were filled with nitrogen and then stoppered and capped.

The stability of the samples was investigated at 25° C. and 40° C., respectively. The indicators were appearance, turbidity, related substances and content. The results are shown in Table 6.

Formula 6-2:

The prescription amount of 0.9 g of acetic acid and 2.7 g of sodium acetate were weighed and dissolved in 400 ml of water for injection, and then added with 12.5 g of mannitol, stirred and dissolved. The above solution was added with 0.1% activated carbon and kept at 60° C. in a water bath for 15 minutes. The mixture was filtered while it was hot to remove activated carbon. The subsequent filtrate was cooled to 20° C. and then continuously purged with nitrogen until the oxygen content of the drug solution is <10%. The solution was then added with the prescription amount of 2.06 g of polyethylene glycol loxenatide, slowly stirred and dissolved under nitrogen atmosphere. The above drug solution was added with water for injection to the constant volume of 500 ml. Finally, the drug solution was filtered by nitrogen pressure filtration through a 0.22 μm microporous membrane and dispensed into vials. The vials were filled with nitrogen and then stoppered and capped. The stability of the samples was investigated at 25° C. and 40° C., respectively. The indicators were appearance, oxygen content, turbidity, related substances and content. The results are shown in Table 6.

TABLE 6

| Formula | Time (Month) | Temperature (° C.) | Appearance | Oxygen content (%) | Turbidity (NTU) | Total impurity (%) | Content (%) |
|---|---|---|---|---|---|---|---|
| 6-1 | 0 | / | Colorless clear liquid | 18.4 | 0.6 | 0.87 | 99.0 |
| 6-2 | | | Colorless clear liquid | 8.4 | 0.5 | 0.92 | 99.3 |
| 6-1 | 6 | 25 | Colorless clear liquid | 19.8 | 0.8 | 1.95 | 98.1 |
| 6-2 | | | Colorless clear liquid | 7.8 | 0.6 | 1.02 | 99.3 |
| 6-1 | 6 | 40 | Colorless clear liquid | 19.2 | 1.3 | 2.90 | 96.7 |
| 6-2 | | | Colorless clear liquid | 8.0 | 0.7 | 1.69 | 98.5 |

What is claimed is:

1. A pharmaceutical composition consisting of polyethylene glycol loxenatide, a buffer, an isosmotic regulator and water, wherein the polyethylene glycol loxenatide has a structure of

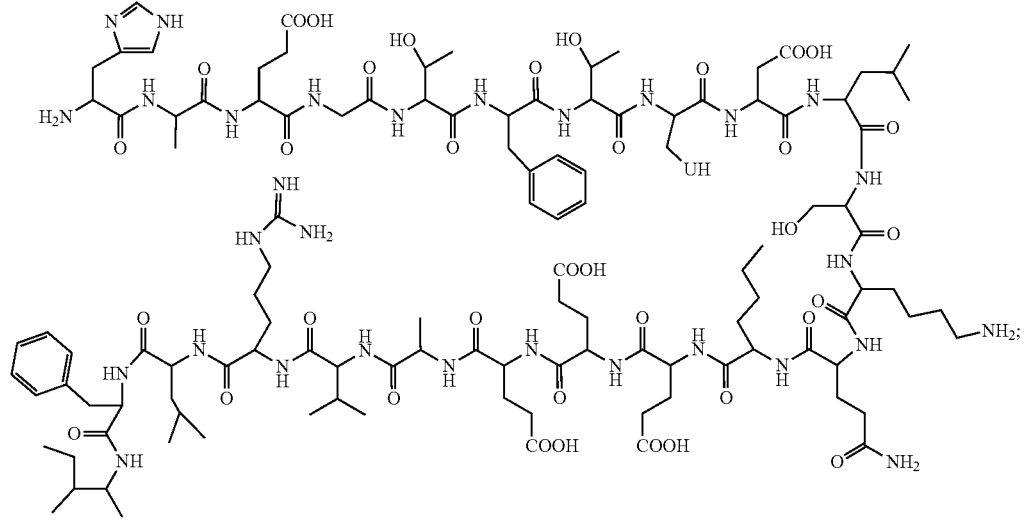

(SEQ ID NO: 1)

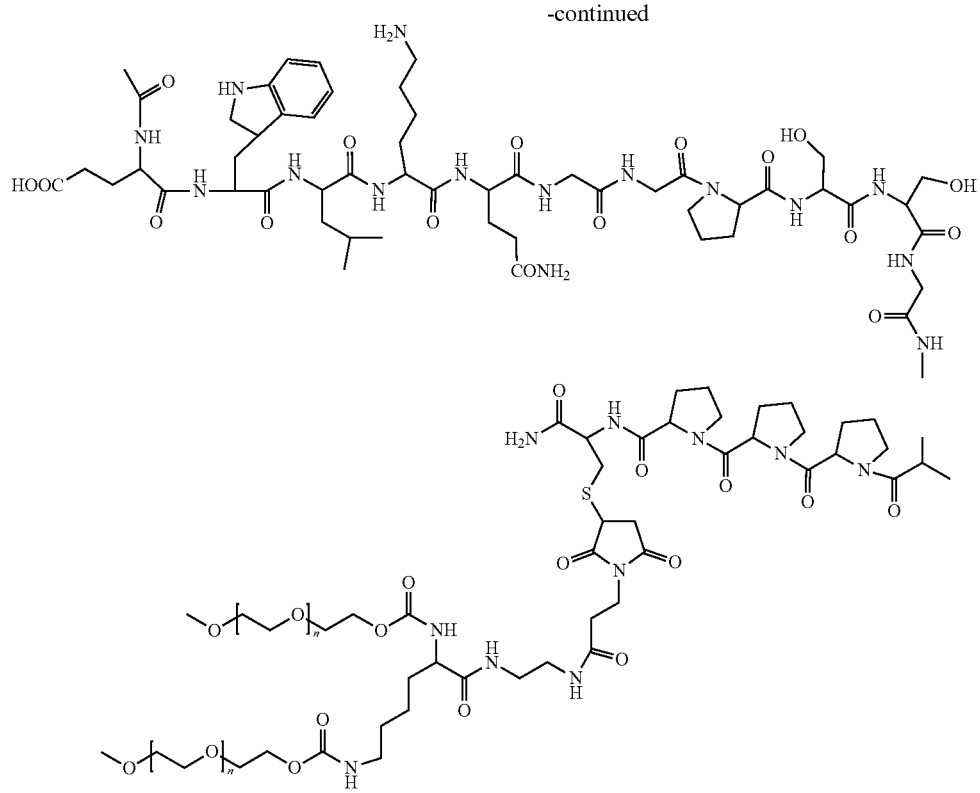

wherein the buffer is an acetate buffer;

the isosmotic regulator is mannitol;

wherein the pharmaceutical composition is in the form of an injection, the injection consisting of 0.1% to 2% (W/V) of polyethylene glycol loxenatide, 0.5% to 1.5% (W/V) of acetic acid/sodium acetate, 2.0% to 5.0% (W/V) of mannitol and water;

wherein the pharmaceutical composition has a pH in the range of 4.0 to 6.0;

wherein the weight ratio of the polyethylene glycol loxenatide to mannitol is 1:1 to 20; and wherein the weight ratio of acetic acid to sodium acetate is 1:2 to 5.

2. The pharmaceutical composition according to claim 1, wherein the weight ratio of the polyethylene glycol loxenatide to the acetic acid/sodium acetate buffer is 1:0.1 to 10.

3. The pharmaceutical composition according to claim 1, wherein the pharmaceutical composition has an oxygen content of ≤10%.

4. The pharmaceutical composition according to claim 1, wherein the weight ratio of the polyethylene glycol loxenatide to the acetic acid/sodium acetate buffer is 1:0.3 to 5.

5. The pharmaceutical composition according to claim 1, wherein the injection consists of 0.1% to 0.5% (W/V) of polyethylene glycol loxenatide, 0.5% to 1.5% (W/V) of acetic acid/sodium acetate, 2.0% to 5.0% (W/V) of mannitol and water.

* * * * *